United States Patent [19]

Heil et al.

[11] Patent Number: 5,849,778
[45] Date of Patent: Dec. 15, 1998

[54] N-PYRAZOLYL ANILINES AS PESTICIDES

[75] Inventors: Markus Heil, Leverkusen; Nobert Lui, Köln; Christoph Erdelen, Leichlingen; Ulrike Wachendorff-Neumann, Neuwied; Heinz-Wilhelm Dehne, Bonn, all of Germany

[73] Assignee: Bayer Aktiengesellschaft, Leverkusen, Germany

[21] Appl. No.: 693,063

[22] PCT Filed: Feb. 6, 1995

[86] PCT No.: PCT/EP95/00416

§ 371 Date: Aug. 12, 1996

§ 102(e) Date: Aug. 12, 1996

[87] PCT Pub. No.: WO95/22530

PCT Pub. Date: Aug. 24, 1995

[30] Foreign Application Priority Data

Feb. 18, 1994 [DE] Germany ............... 44 05 207.3

[51] Int. Cl.⁶ .................. A61K 31/415; C07D 231/52
[52] U.S. Cl. .................. 514/403; 548/368.7; 548/371.7; 548/371.4

[58] Field of Search ............... 514/403; 548/368.7, 548/371.7, 371.4

[56] References Cited

PUBLICATIONS

CA111:232751 Chakrabarti et al.,1989.

*Primary Examiner*—Jane Fan
*Attorney, Agent, or Firm*—Sprung Kramer Schaefer & Briscoe

[57] ABSTRACT

The present invention relates to new N-pyrazolylanilines and N-pyrazolylaminopyridines of the formula (I)

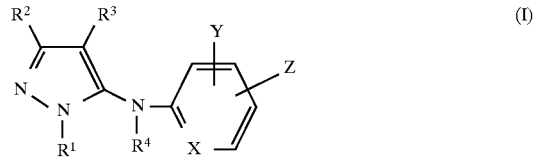

in which
$R^1, R^2, R^3, R^4, X, Y$ and $Z$ have the meanings given in the description, to processes for their preparation, and to their use as pesticides.

9 Claims, No Drawings

N-PYRAZOLYL ANILINES AS PESTICIDES

This application is a 371 of PCT/EP95/00416, Feb. 6, 1995 now WO95/22,530.

The present invention relates to new N-pyrazolylanilines and N-pyrazolylaminopyridines, to processes for their preparation, and to their use as pesticides.

It is known that certain N-heteroaryl-2-nitro-anilines such as, for example, N-[1,3-dimethylpyrazol-5-yl]-2,6-dinitro-4-trifluoromethylaniline and N-[5-trifluoro-methyl-1,3,4-thiadiazol-2-yl]-2,6-dinitro-4-trifluoro-methylaniline, have fungicidal and insecticidal properties (cf. EP-A-0 478 974, WO 93/19 054). However, the activity of these compounds is not always entirely satisfactory under certain circumstances, in particular when low concentrations of active compound and low application rates are used.

New N-pyrazolylanilines and N-pyrazolylaminopyridines of the formula (I)

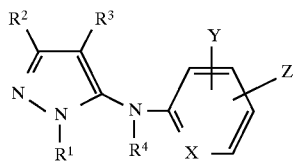

have now been found, in which

X represents C—$NO_2$, C-halogen, C-halogenoalkyl or N,
Y represents $NO_2$, CN, halogen or halogenoalkyl,
Z represents $NO_2$, halogen, halogenoalkyl, halogenoalkoxy or halogenoalkylthio,
$R^1$ represents hydrogen, or in each case optionally substituted alkyl, alkenyl, alkinyl, aryl, hetaryl or aralkyl,
$R^2$ and $R^3$ independently of one another represent hydrogen, halogen, cyano or nitro, or in each case optionally substituted alkyl, aryl or hetaryl, or one of the radicals $CO_2R^5$, $CONR^6R^7$, $CSNR^6R^7$, $S(O)_nR^8$,
$R^4$ represents halogen, in each case optionally substituted alkyl, alkenyl, alkinyl, aralkyl, aryloxy or aralkyloxy or one of the radicals $SO_2NR^6R^7$, $SO_2R^9$, $COR^{10}$ or $CH_2N(R^9)_w$, in which
  w represents $CO_2R^5$ or $SO_2R^5$,
  $R^5$ represents alkyl,
  $R^6$ and $R^7$ independently of one another represent hydrogen or alkyl, or together with the N atom to which they are bonded form a ring which optionally contains at least one further hetero atom,
  $R^8$ represents alkyl or halogenoalkyl,
  $R^9$ represents alkyl or optionally substituted aryl,
  $R^{10}$ represents alkyl, alkoxy, or in each case optionally substituted aryl or aryloxy, and
  n represents 0, 1 or 2,
with the proviso that
  $R^1$ does not represent alkyl, optionally substituted phenyl, optionally substituted phenylsulfonyl or pyridyl and/or
  $R^2$ does not represent hydrogen, alkyl or phenyl and/or
  $R^3$ does not represent hydrogen, CN, halogen, optionally substituted phenyl, optionally substituted phenylsulfonyl, $CO_2$-alkyl or $CO_2$-benzyl,
if
  $R^4$ represents hydrogen and simultaneously
  X represents C—$NO_2$ and simultaneously one of the substituents
  Y or Z represents halogenoalkyl and the other substituent represents $NO_2$.

Furthermore, it has been found that A) the N-pyrazolylanilines and N-pyrazolylaminopyridines of the formula (I) are obtained by a process which comprises reacting 5-aminopyrazoles of the formula (II)

in which $R^1$, $R^2$ and $R^3$ have the abovementioned meanings with compounds of the formula (III)

in which

Hal represents fluorine, chlorine, bromine or iodine, preferably fluorine or chlorine, and
X, Y and Z have the abovementioned meaning in the presence of a base and in the presence of a diluent, and, if appropriate, subsequently reacting the resulting compounds of the formula (Ia)

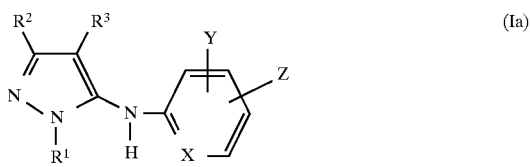

in which

X, Y, Z, $R^1$, $R^2$ and $R^3$ have the abovementioned meanings with compounds of the formula (IV)

in which

V represents an anionic leaving group such as, for example, chlorine, bromine, iodine, acetoxy, tosyl or mesyl and
$R^{11}$ has the meaning mentioned above for $R^4$ with the exception of hydrogen in the presence of a base and if appropriate in the presence of a diluent, and that B) compounds of the formula (Ib)

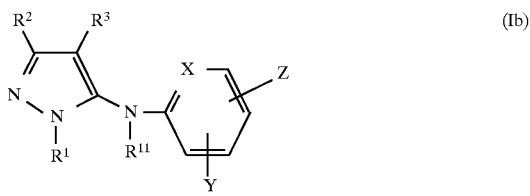

in which $R^1$, $R^2$, $R^3$, X, Y and Z have the abovementioned meanings and
$R^{11}$ has the abovementioned meaning are obtained by a process which comprises reacting 5-aminopyrazoles of the formula (II)

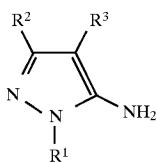

(II)

in which
R[1], R[2] and R[3] have the abovementioned meanings with compounds of the formula (IV)

$$R^{11}-V \quad (IV)$$

in which
R[11] and V have the abovementioned meanings in the presence of a base and in the presence of a diluent, and subsequently reacting the resulting compounds of the formula (V)

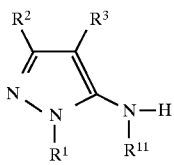

(V)

in which
R[1], R[2], R[3] and R[11] have the abovementioned meanings with compounds of the formula (III)

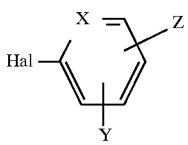

(III)

in which
Hal, X, Y and Z have the abovementioned meanings in the presence of a base and in the presence of a diluent.

The new compounds of the formula (I) have properties which allow them to be used as pesticides. In particular, they can be used as insecticides, arthropodicides and fungicides.

Formula (I) provides a general definition of the N-pyrazolylanilines and N-pyrazolylaminopyridines according to the invention.

Preferred substituents or ranges of the radicals listed in the formulae mentioned hereinabove and hereinbelow will be illustrated in the following text.

X preferably represents C—NO$_2$, C-halogen, C—C$_1$–C$_6$-halogenoalkyl or N.

Y preferably represents NO$_2$, CN, halogen or C$_1$–C$_6$-halogenoalkyl.

Z preferably represents NO$_2$, halogen, C$_1$–C$_6$-halogenoalkyl, C$_1$–C$_6$-halogenoalkoxy or C$_1$–C$_6$-halogenoalkylthio.

R[1] preferably represents hydrogen, C$_1$–C$_8$-alkyl, C$_1$–C$_8$-cyanoalkyl, C$_1$–C$_8$-halogenoalkyl, C$_1$–C$_8$-hydroxyalkyl, C$_1$–C$_4$-alkoxy-C$_1$–C$_8$-alkyl, or represents phenyl, benzyl or phenethyl, each of which is optionally monosubstituted to trisubstituted by identical or different substituents from the series consisting of halogen, C$_1$–C$_4$-alkyl, C$_1$–C$_4$-halogenoalkyl, C$_1$–C$_4$-alkoxy, C$_1$–C$_4$-halogenoalkoxy, C$_1$–C$_4$-alkylthio, C$_1$–C$_4$-halogenoalkylthio, phenyl, phenoxy, CN or NO$_2$, or represents pyridyl which is monosubstituted to trisubstituted by identical or different substituents from the series consisting of halogen, C$_1$–C$_4$-alkyl, C$_1$–C$_4$-alkoxy or C$_1$–C$_4$-halogenoalkyl, or represents pyrimidyl, thiadiazolyl or thiazolyl, each of which is optionally monosubstituted or disubstituted by identical or different substituents from the series consisting of halogen, C$_1$–C$_4$-alkyl, C$_1$–C$_4$-alkoxy or C$_1$–C$_4$-halogenoalkyl.

R[2] and R[3] independently of one another preferably represent hydrogen, halogen, cyano, nitro, C$_1$–C$_8$-alkyl, C$_1$–C$_8$-halogenoalkyl, C$_1$–C$_8$-hydroxyalkyl, C$_1$–C$_4$-alkoxy-C$_1$–C$_8$-alkyl, or represent phenyl or thienyl, each of which is optionally monosubstituted to trisubstituted by identical or different substituents from the series consisting of halogen, C$_1$–C$_4$-alkyl, C$_1$–C$_4$-alkoxy, C$_1$–C$_4$-halogenoalkyl or C$_1$–C$_4$-halogenoalkylthio, or represent one of the radicals CO$_2$R[5], CONR[6]R[7], CSNR[6]R[7], S(O)$_n$R[8].

R[4] represents hydrogen, C$_1$–C$_8$-alkyl, C$_1$–C$_8$-halogenoalkyl, C$_1$–C$_8$-hydroxyalkyl, C$_1$–C$_4$-alkoxy-C$_1$–C$_8$-alkyl, C$_3$–C$_8$-alkenyl, C$_3$–C$_8$-halogenoalkenyl, C$_3$–C$_8$-hydroxyalkenyl, C$_1$–C$_4$-alkoxy-C$_3$–C$_8$-alkenyl, C$_3$–C$_8$-alkinyl, C$_3$–C$_8$-halogenoalkinyl, C$_3$–C$_8$-hydroxyalkinyl, C$_1$–C$_4$-alkoxy-C$_3$–C$_8$-alkinyl, or represents phenoxy, benzyl or benzyloxy, each of which is optionally monosubstituted to trisubstituted by identical or different substituents from the series consisting of halogen, C$_1$–C$_4$-alkyl, C$_1$–C$_4$-alkoxy, C$_1$–C$_4$-halogenoalkyl or C$_1$–C$_4$-halogenoalkoxy, or represents one of the radicals SO$_2$R[9], COR[10], CH$_2$—N(R[9])w, SO$_2$NR[6]R[7].

w preferably represents CO$_2$R[5] or SO$_2$R[5].

R[5] preferably represents C$_1$–C$_8$-alkyl.

R[6] and R[7] independently of one another preferably represent hydrogen, C$_1$–C$_8$-alkyl, or together with the N atom to which they are bonded are 5- to 7-membered ring which optionally contains up to two additional hetero atoms from the series consisting of N, O and S.

R[8] preferably represents C$_1$–C$_8$-alkyl or C$_1$–C$_8$-halogenoalkyl.

R[9] preferably represents C$_1$–C$_8$-alkyl, or represents phenyl which is optionally monosubstituted to trisubstituted by identical or different substituents from the series consisting of halogen, C$_1$–C$_4$-alkyl or C$_1$–C$_4$-alkoxy.

R[10] preferably represents C$_1$–C$_8$-alkyl or C$_1$–C$_8$-alkoxy, or represents phenyl or phenoxy, each of which is optionally monosubstituted to trisubstituted by halogen, C$_1$–C$_4$-alkyl or C$_1$–C$_4$-alkoxy.

n preferably represents 0, 1 or 2.

X particularly preferably represents C—NO$_2$, C-fluoro, C-chloro, C-bromo, C$_1$–C$_3$-halogenoalkyl having 1 to 5 identical or different halogen atoms from the series consisting of fluorine, chlorine and bromine, or represents N.

Y particularly preferably represents NO$_2$, CN, fluorine, chlorine, bromine or C$_1$–C$_4$-halogenoalkyl having 1 to 7 identical or different halogen atoms from the series consisting of fluorine, chlorine and bromine.

Z particularly preferably represents NO$_2$, fluorine, chlorine, bromine, C$_1$–C$_4$-halogenoalkyl, C$_1$–C$_4$-halogenoalkoxy or C$_1$–C$_4$-halogenoalkylthio, each of which has 1 to 7 identical or different halogen atoms from the series consisting of fluorine, chlorine and bromine.

R[1] particularly preferably represents C$_1$–C$_6$-alkyl, C$_1$–C$_6$-cyanoalkyl, C$_1$–C$_6$-halogenoalkyl having one to three identical or different halogen atoms from the series consisting of fluorine, chlorine and bromine, or represents $C_1$–$C_6$-hydroxyalkyl, $C_1$–$C_2$-alkoxy-$C_1$–$C_6$-alkyl, or represents phenyl, benzyl or phenethyl, which in each case is optionally monosubstituted to trisubstituted by identical or different substituents from the series consisting of fluorine, chlorine, bromine, $C_1$–$C_3$-alkyl, $C_1$–$C_3$-alkoxy, $C_1$–$C_3$-halogenoalkyl, $C_1$–$C_3$-halogenoalkoxy or $C_1$–$C_4$-halogenoalkylthio, each of which has one to three identical or different halogen atoms from the series consisting of fluorine, chlorine and bromine, or CN or nitro, or represents pyridyl which is monosubstituted to trisubstituted by identical or different substituents from the series consisting of fluorine, chlorine, bromine, $C_1$–$C_3$-alkyl, $C_1$–$C_3$-alkoxy or $C_1$–$C_3$-halogenoalkyl having one to three identical or different halogen atoms from the series consisting of fluorine, chlorine and bromine, or represents pyrimidyl or thiadiazolyl, each of which is optionally monosubstituted or disubstituted by identical or different substituents from the series consisting of fluorine, chlorine, bromine, $C_1$–$C_3$-alkyl, $C_1$–$C_3$-alkoxy or $C_1$–$C_3$-halogenoalkyl having one to three identical or different halogen atoms from the series consisting of fluorine, chlorine and bromine.

$R^2$ and $R^3$ independently of one another particularly preferably represent hydrogen, fluorine, chlorine, bromine, CN, $C_1$–$C_6$-alkyl, $C_1$–$C_6$-halogenoalkyl having one to six identical or different halogen atoms from the series consisting of fluorine, chlorine and bromine, or represent $C_1$–$C_2$-alkoxy-$C_1$–$C_6$-alkyl, or represent phenyl or thienyl, each of which is optionally monosubstituted to trisubstituted by identical or different substituents from the series consisting of fluorine, chlorine, bromine, $C_1$–$C_3$-alkyl or $C_1$–$C_3$-alkoxy, or represent one of the radicals $CO_2R^5$, $CONR^6R^7$, $CSNR^6R^7$, $S(O)_nR^8$.

$R^4$ particularly preferably represents hydrogen, or represents $C_1$–$C_6$-alkyl, $C_3$–$C_6$-alkenyl or $C_3$–$C_6$-alkinyl, each of which is optionally substituted by one to three halogen atoms from the series consisting of fluorine, chlorine and bromine, or represents $C_1$–$C_4$-alkoxymethyl, or represents benzyl or benzyloxy, each of which is optionally monosubstituted or disubstituted by fluorine, chlorine or bromine, or represents one of the radicals $SO_2R^9$, $COR^{10}$, $CH_2$—$N(R^9)CO_2R^5$.

$R^5$ particularly preferably represents $C_1$–$C_4$-alkyl.

$R^6$ and $R^7$ independently of one another particularly preferably represent hydrogen, methyl or ethyl.

$R^8$ particularly preferably represents $C_1$–$C_4$-alkyl or $C_1$–$C_4$-halogenoalkyl having one to three fluorine and/or chlorine atoms.

$R^9$ particularly preferably represents $C_1$–$C_4$-alkyl, or represents phenyl which is optionally monosubstituted to trisubstituted by fluorine, chlorine and/or bromine.

$R^{10}$ particularly preferably represents $C_1$–$C_4$-alkyl, or represents phenyl which is optionally monosubstituted to trisubstituted by fluorine, chlorine and/or bromine.

n particularly preferably represents 0, 1 or 2.

X very particularly preferably represents C—$NO_2$, C—Cl or N.

Y very particularly preferably represents $N_2$, CN, fluorine, chlorine or $CF_3$.

Z very particularly preferably represents $NO_2$, fluorine, chlorine, $CF_3$, $OCF_3$ or $SCF_3$.

$R^1$ very particularly preferably represents methyl, ethyl, n- or i-propyl, n-butyl, i-butyl, s-butyl, t-butyl, the isomeric pentyls or isomeric hexyls, each of which is optionally monosubstituted to trisubstituted by fluorine and/or chlorine or monosubstituted by cyano or represents phenyl, benzyl or phenethyl each of which is optionally monosubstituted to trisubstituted by identical or different substituents from the series consisting of fluorine, chlorine, bromine, $CF_3$, $OCF_3$, $SCF_3$, CN and $NO_2$, or represents pyridyl, pyrimidyl or thiadiazolyl, each of which is optionally monosubstituted to trisubstituted by identical or different substituents from the series consisting of fluorine, chlorine, bromine or $CF_3$.

$R^2$ and $R^3$ independently of one another very particularly preferably represent hydrogen, chlorine, bromine, CN, methyl, ethyl, n-propyl, i-propyl, n-butyl, t-butyl, $CF_3$, $C_2F_5$ or $CH_2OCH_3$, or represent phenyl which is optionally monosubstituted to trisubstituted by identical or different substituents from the series consisting of fluorine, chlorine, bromine, methyl and methoxy, or represent one of the radicals $CO_2R^5$, $CONR^6R^7$ or $S(O)_nR^8$.

$R^4$ very particularly preferably represents hydrogen, methyl, ethyl, 2-propenyl, 2-propinyl, methoxymethyl, ethoxymethyl, propoxymethyl, i-propoxymethyl or n-butoxymethyl.

$R^5$ very particularly preferably represents methyl or ethyl.

$R^6$ and $R^7$ very particularly preferably represent hydrogen.

$R^8$ very particularly preferably represents methyl, ethyl, trifluoromethyl, 1,1-difluoroethyl or 2,2,2-trifluoroethyl.

n very particularly preferably represents 0, 1 or 2.

The following applies in each case:

$R^1$ does not represent alkyl, optionally substituted phenyl, optionally substituted phenylsulfonyl or pyridyl and/or $R^2$ does not represent hydrogen, alkyl or phenyl and/or $R^3$ does not represent hydrogen, CN, halogen, optionally substituted phenyl, optionally substituted phenylsulfonyl, $CO_2$-alkyl or $CO_2$-benzyl, if $R^4$ represents hydrogen and simultaneously X represents C—$NO_2$ and simultaneously one of the substituents Y or Z represents halogenoalkyl and the other substituent represents $NO_2$.

A preferred group of compounds are compounds of the formula (I-1)

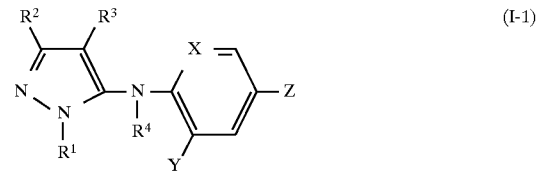

(I-1)

in which $R^1$, $R^2$, $R^3$, $R^4$, X, Y and Z have the above mentioned meanings, with the proviso that $R^1$ does not represent alkyl, optionally substituted phenyl, optionally substituted phenylsulfonyl or pyridyl and/or $R^2$ does not represent hydrogen, alkyl or phenyl and/or $R^3$ does not represent hydrogen, CN, halogen, optionally substituted phenyl, optionally substituted phenylsulphonyl, $CO_2$-alkyl or $CO_2$-benzyl, if
- $R^4$ represents hydrogen or simultaneously
- X represents C—$NO_2$ and simultaneously one of the substituents
- Y or Z represents halogenoalkyl and the other substituent represents $NO_2$.

A particularly preferred group of compounds are compounds of the formula (I-2)

[Structure (I-2)]

in which
- $X^1$ has the above mentioned meanings given for X with the exception of C—$NO_2$ and
- $R^1$, $R^2$, $R^3$, $R^4$, Y and Z have the above mentioned meanings, with the proviso that
- Y does not represent $NO_2$ if Z represents $NO_2$.

A very particularly preferred group of compounds are compounds of the formula (I-3)

[Structure (I-3)]

in which
- $X^1$ has the above mentioned meaning,
- $Y^1$ has the above mentioned meanings given for Y with the exception of $NO_2$ and
- $R^1$, $R^2$, $R^3$, $R^4$ and Z have the above mentioned meanings.

The definitions of radicals or illustrations mentioned above in general or in preferred ranges can be combined as desired with each other, that is to say combinations between each of the ranges and preferred ranges are also possible. They apply to the end products and analogously to the precursors and intermediates.

Compounds of the formula (I), (I-1), (I-2) and (I-3) which are preferred according to the invention are those which in each case contain a combination of the meanings listed above as being preferred (preferable).

Compounds of the formula (I), (I-1), (I-2) and (I-3) which are particularly preferred according to the invention are those which in each case contain a combination of the meanings listed above as being particularly preferred.

Compounds of the formula (I), (I-1), (I-2) and (I-3) which are very particularly preferred according to the invention are those which in each case contain a combination of the meanings listed above as being very particularly preferred.

The hydrocarbon radicals such as alkyl which have been mentioned above in the definition of the compounds according to the invention are, as far as this is possible, in each case straight-chain or branched, also in connection with hetero atoms, such as alkoxy.

If, for example, 1-methyl-3-thiomethyl-4-cyano-5-aminopyrazole, 1-chloro-2,6-dinitro-4-trifluoromethylbenzene and chloromethyl ethyl ether are used as starting substances, the course of the reaction of process A) according to the invention can be represented by the following equation:

[Reaction scheme A showing three steps with -HCl, $ClCH_2OC_2H_5$/-HCl]

if, for example, 1-methyl-3-pentafluoroethyl-4-trifluoromethyl-5-aminopyrazole, iodomethane and 2-chloro-4-trifluoromethyl-2,6-dinitrobenzene are used as starting substances, the course of the reaction of process B) according to the invention can be represented by the following equation:

[Reaction scheme B showing steps with $ICH_3$/-HI and -HCl]

The 5-aminopyrazoles of the formula (II) required as starting substances for carrying out the process according to the invention are known and/or can be prepared by known processes (cf., for example, Chem. Het. Comp. 17 (1981), 1; J. Org. Chem. 21 (1956), 1240; EP 0 201 852; EP 0 392 241; Chem. Ber. 95 (1962), 2871; J. Org. Chem. 29 (1964) 1915; Isv. Attad. Nauk SSR, Ser. Khim 11 (1990) 2583; J. Chem. Research (5), 1993, 76).

The compounds of the formula (III) which are required as starting substances for carrying out the process according to the invention are known and/or can be prepared by known methods (cf., for example, EP 0 398 499, J. Org. Chem. 47 (1982) 2856; U.S. Pat. No. 3,888,932; U.S. Pat. No. 3,928, 416).

The compounds of the formula (IV) which are required as starting substances for carrying out the process according to the invention are known substances of organic chemistry.

The following information on the process according to the invention applies in each case to both steps of Preparation Alternatives A) and B).

The process according to the invention for the preparation of the new compounds of the formula (I) is preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulfoxide, tetramethylene sulfone and hexamethylphosphoric triamide.

Bases which can be employed in the process according to the invention are all acid-binding agents which can conventionally be used for reactions of this type. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate, sodium hydrogen carbonate, potassium carbonate or potassium hydrogen carbonate and also calcium carbonate, alkali metal acetates, such as sodium acetate and potassium acetate, alkali metal alcoholates, such as sodium tert-butylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo [2,2,2]-octane (DABCO).

The reaction temperatures in the process according to the invention can be varied within a substantial range. In general, the process is carried out at temperatures between 0° C. and 100° C., preferably at temperatures between 10° C. and 80° C.

The process according to the invention is generally carried out under atmospheric pressure. However, it can also be carried out under elevated or reduced pressure.

To carry out the process according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the temperature required in each case. Working-up in the process according to the invention is carried out in each case by customary methods (cf. Preparation Examples).

The compounds of the formula (I) according to the invention can be employed as pesticides. Pests are undesired animal pests, in particular insects and mites, which are harmful to plants or higher animals.

The active compounds according to the invention are suitable for combating animal pests, preferably arthropods, in particular insects and arachnids, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp.

From the order of the Anoplura, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi, Phylloxera vastatrix,* Pemphigus spp., Empoasca spp., *Euscelis bilobatus, Nephotettix cincticeps, Lecaniuh corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana*, Heliothis spp., *Spodoptera exigua, Mamestra brassicae, Panolis flanmmea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychu spp., Hemitarsonemus spp.

The active compounds according to the invention also have a fungicidal activity and can be employed as fungicides in plant protection, for example against the causative organism of rice blast disease (*Pyricularia oryzae*).

Fungicidal agents are employed in plant protection for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, Pyrenophora teres or *P. graminea* (conidia form: Drechslera, synonym: Helminthosporium);

Cochliobolus species, such as, for example, *Cochliobolus sativus* (conidia form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particular success for combating diseases in fruit and vegetable growing such as, for example, against the causative organism of apple scab (Venturia inaequalis). Besides, the active compounds according to the invention have a good in-vitro activity.

For use as insecticides, acaricides and fungicides the active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The following may be mentioned as insecticides:

acrinathrin, alphamethrin, betacyfluthrin, bifenthrin, brofenprox, cis-resmethrin, clocythrin, cycloprothin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, Alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecasrb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlofenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mevinphos, mesulfenphos, methacrifos, methamidophos, methidathion, monocrotophos, naled, omethoate, oxydemethon M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphention, quinalphos, salithion, sebufos, sulfotep, sulprofos, tetrachlorvinphos, temephos, thiomethon, thionazin, trichlorfon, triazophos, vamidothion, buprofezin, lufenuron, chlorfluazuron, diflubenzuron, flucycloxuron, flufenoxuron, hexaflumuron, pyriproxifen, tebufenozide, teflubenzuron, triflumuron, imidacloprid, nitenpyram, abamectin, amitraz, avermectin, azadirachtin, bensultap, Bacillus thuringiensis, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethoprophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenthiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, phosalone, profenofos, pyraclofos, pyridaben, pyrimidifen, tebufenpyrad, thuringiensin, triarathene, triazophos, the compound of the formula

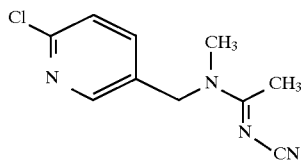

and the compound of the formula

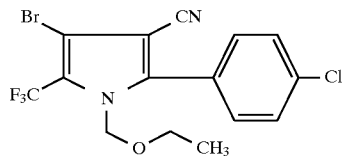

The following may be mentioned as fungicides:

sulfenamides, such as dichlorofluanide (Euparen), tolylfluanide (Methyleuparen), folpet, fluorofolpet;

benzimidazoles, such as carbendazim (MBC), benomyl, fuberidazole, thiabendazole or their salts;

thiocyanates such as thiocyanatomethylthiobenzothiazole (TCMTB), methylene bisthiocyanate (MBT);

quaternary ammonium compounds, such as benzyldimethyltetradecylammonium chloride, benzyl-dimethyldodecylammonium chloride, dodecyl-dimethyl ammonium chloride;

morpholine derivatives, such as $C_{11}$–$C_{14}$-4-alkyl-2,6-dimethyl-morpholine homologs (tridemorph), (±)-cis-4-[tert-butylphenyl)-2-methylpropyl]-2,6-dimethylmorpholine (fenpropimorph), falimorph;

phenols, such as o-phenylphenol, tribromophenol, tetrachlorophenol, pentachlorophenol, 3-methyl-4-chlorophenol, dichlorophene, chlorophene or their salts;

azoles, such as triadimefon, triadimenol, bitertanol, tebuconazole, propiconazole, azaconazole, hexaconazole, prochloraz, cyproconazole, 1-(2-chlorophenyl)-2-(1-chlorocyclopropyl)-3-(1,2,4-triazol-1-yl)-propan-2-ol or 1-(2-chlorophenyl)-2-(1,2,4-triazol-1-yl-methyl)-3,3-dimethyl-butan-2-ol;

iodopropargyl derivatives such as iodopropargyl butylcarbamate (IPBC), iodopropargyl chlorophenyl formal, iodopropargyl phenylcarbamate, iodopropargyl hexylcarbamate, iodopropargyl cyclohexylcarbamate, iodopropargyloxyethyl phenylcarbamate;

iodine derivatives such as diiodomethyl-p-aryl sulfones, for example diiodomethyl-p-tolyl sulfone;

bromine derivatives such as bromopol;

isothiazolines such as N-methylisothiazolin-3-one, 5-chloro-N-methylisothiazolin-3-one, 4,5-dichloro-N-octylisothiazolin-3-one, N-octylisothiazolin-3-one (octilinone);

benzoisothiazolinones, cyclopenteneisothiazolines;

pyridines, such as 1-hydroxy-2-pyridinethione (and their sodium, iron, manganese or zinc salts), tetrachloro-4-methylsulfonylpyridine;

metal soaps, such as tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate, oxides, such as TBTO, $Cu_2O$, CuO, ZnO;

organotin compounds, such as tributyltin naphthenate and tributyltin oxide;

dialkyldithiocarbamates, such as sodium and zinc salts of dialkyldithiocarbamates, tetramethylthiuram disulfide (TMTD);

nitrites such as 2,4,5,6-tetrachloroisophthalonitrile (chlorthalonil) and other microbicides having an activated halogen group, such as Cl-Ac, MCA, tectamer, bromopol, bromidox;

benzothiazoles, such as 2-mercaptobenzothiazoles; dazomet;

quinolines, such as 8-hydroxyquinoline;

formaldehyde-releasing compounds, such as benzyl alcohol mono(poly)hemiformal, oxazolidines, hexahydro-s-triazines, N-methylchloroacetamide;

tris-N-(cyclohexyldiazeniumdioxy)-aluminum, N-(cyclohexyldiazeniumdioxy)-tributyltin or K salts, bis-(N-cyclohexyl)diazenium-(dioxy-copper or -aluminum).

The active compounds according to the invention can also be present in their commercially available formulations and in the use forms prepared from these formulations in a mixture with synergists. Synergists are compounds by means of which the action of the active compounds is increased without the synergist added having to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The compounds according to the invention are also specially suitable for the treatment of vegetative and generative propagation material such as, for example, seeds of cereals, maize, vegetables and the like, or of bulbs, cuttings and the like.

When used against hygiene pests and pests of stored products, the active compounds are distinguished by an excellent residual action on wood and clay as well as a good stability to alkali on limed substrates.

The active compounds can be employed as such, in the form of their formulations or in the use forms prepared therefrom by further dilution, such as ready-to-use solutions, suspensions, emulsions, powders, pastes and granules. They are applied in the customary manner, for example by pouring, spraying, atomizing, scattering.

The active compound according to the invention can be applied before or after emergence of the plants.

They can also be incorporated into the soil before sowing.

The amount of active compound applied can vary within wide limits. It depends essentially on the nature of the desired effect. In general, application rates are between 10 g and 10 kg of active compound per hectare of soil surface, preferably between 50 g and 5 kg per ha.

To prepare the pesticides, the active compounds according to the invention, depending on their particular physical and/or chemical properties, can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example ligninsulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention are not only active against plant, hygiene and stored product pests, but also, in the veterinary medicine sector, against animal ectoparasites such as scaly ticks, argasidae, scab mites, trombidae, flies (stinging and sucking), parasitic fly larvae, lice, hair lice, bird lice and fleas. For example, they have an outstanding activity against ticks such as, for example, *Boophilus microplus*.

The active compounds of the formula (I) according to the invention are also suitable for the combating of arthropods which infest useful animals in agriculture such as, for example, cattle, sheep, goats, horses, pigs, donkeys, camels, buffalo, rabbits, hens, turkeys, ducks, geese, bees, other domestic animals such as, for example, dogs, cats, cage birds, aquarium fish and so-called experimental animals such as, for example, hamsters, guinea pigs, rats and mice. The aim of combating these arthropods is to reduce fatalities and reductions in yield (in meat, milk, wool, skins, eggs, honey, etc.) so that the use of the active compound according to the invention renders the keeping of animals more economic and more simple.

In the veterinary sector the active compounds according to the invention are employed in a known manner by enteral administration in the form of, for example, tablets, capsules, potions, drenches, granules, pastes, boli, by the feed-through method, suppositories, by parenteral administration, for example by injection (intramuscular, subcutaneous, intravenous, intraperitoneal etc.), by implants, by nasal administration, by dermal application in the form, for example, of dipping or bathing, spraying, pouring on and spotting on, washing, dusting and with the aid of shaped articles which contain active compound, such as neck bands, ear tags, tail tags, limb bands, halters, marking devices and the like.

The compositions according to the invention, besides at least one compound of the general formula (I) and, if appropriate, besides extenders and auxiliaries, preferably comprise at least one surfactant.

Unless otherwise specified, all percentages are by weight.

The preparation of the compounds of the formula (I) according to the invention will be illustrated by the Preparation Examples which follow.

PREPARATION EXAMPLES

Example 1

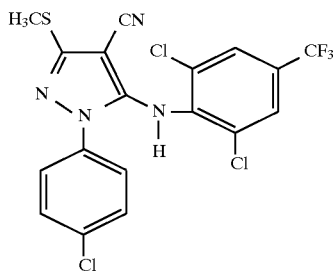

1.2 g (0.04 mol) of NaH (80% dispersion in mineral oil) are introduced into 20 ml of DMF, and a solution of 5.3 g (0.02 mol) of 1-(4-chlorophenyl)-3-thiomethyl-4-cyano-5-aminopyrazole is added. 5.0 g (0.02 mol) of 3,4,5-trichlorobenzotrifluoride are added, and the mixture is heated for 18 hours at 80° C. The reaction mixture is poured into 300 ml of ice-water to which 10 ml of glacial acetic acid have been added and this mixture is subseqently extracted using dichloromethane (3×100 ml). The combined organic phases are dried, the solvent is removed under reduced pressure, and the residue is chromatographed on silica gel using dichloromethane as the eluent. 4.5 g (47% of theory) of N-[1-(4-chlorophenyl)-3-thiomethyl-4-cyanopyrazol-5-yl]-2,6-dichloro-4-trifluoromethylaniline are obtained.

M.p.: 135° C.

Example 2

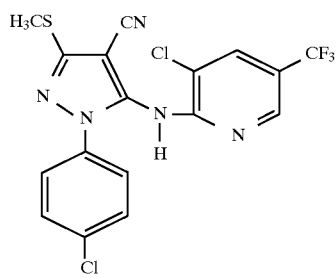

1.14 g (0.038 mol) of NaH (80% dispersion in mineral oil) are introduced into 100 ml of THF and 6.0 g (0.019 mol) of 1-(4-chlorophenyl)-3-thiomethyl-4-cyano-5-aminopyrazole are added in portions. 4.3 g (0.020 mol) of 2,3-dichloro-5-trifluoromethylpyridine are subsequently added dropwise, and the mixture is refluxed for 18 hours. The reaction mixture is cooled and poured into 300 ml of ice-water to which 10 ml of glacial acetic acid have been added, and the yellow precipitate is filtered off with suction. 6.5 g (75% of theory) of N-[1-(4-chlorophenyl)-3-thiomethyl-4-cyanopyrazol-5-yl]-2-amino-3-chloro-5-trifluoromethylpyridine are obtained.

M.p.: 194° C.

Example 3

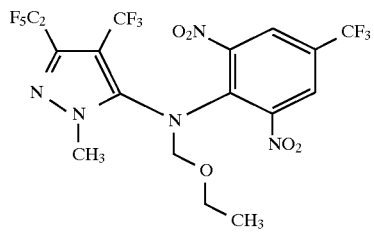

0.35 g (0.0116 mol) of NaH (80% dispersion in mineral oil) is introduced into 50 ml of THF, and 3.0 g (0.0058 mol) of N-(1-methyl-3-pentafluoroethyl-4-trifluoromethylpyrazol-5-yl) -2,6-dinitro-4-trifluoromethylaniline in 10 ml of THF and 1.1 g (0.0116 mol) of chloromethyl ethyl ether are added in succession. The reaction mixture is refluxed for 2 hours, cooled and poured into 400 ml of ice-water. The precipitate which has separated out is filtered off with suction and dried. 2.9 g (86% of theory) of N-ethoxymethyl-N-(1-methyl-3-pentafluoroethyl-4-trifluoromethylpyrazol-5-yl)-2,6-dinitro-4-trifluoromethylaniline is obtained.

M.p.: 103° C.

The following compounds of the formula (I-1) are obtained analogously and in accordance with the general information instructions:

TABLE 1

(I-1)

[Structure: pyrazole with R¹ on N, R² and R³ on pyrazole ring, N(R⁴) linker to phenyl ring bearing X, Y, Z substituents]

| Ex. No. | R¹ | R² | R³ | R⁴ | X | Y | Z | M.p. (°C.) |
|---|---|---|---|---|---|---|---|---|
| 4 | C₆H₅* | SCH₃ | CN | H | C—NO₂ | NO₂ | CF₃ | 163 |
| 5 | C₆H₅ | SCH₃ | CN | H | C—NO₂ | CF₃ | NO₂ | 80 |
| 6 | C₆H₅ | SCH₃ | CN | H | C—Cl | Cl | CF₃ | 120 |
| 7 | C₆H₅ | SCH₃ | CN | H | C—Cl | CN | CF₃ | 122 |
| 8 | C₆H₅ | SCH₃ | CN | H | C—Cl | F | CF₃ | Resin |
| 9 | C₆H₅ | SCH₃ | CN | H | N | Cl | CF₃ | 83 |
| 10 | 4-Cl-C₆H₄ | SCH₃ | CN | H | C—NO₂ | NO₂ | CF₃ | 212 |
| 11 | 4-Cl-C₆H₄ | SCH₃ | CN | H | C—Cl | Cl | CF₃ | 135 |
| 12 | 4-Cl-C₆H₄ | SCH₃ | CN | H | C—Cl | CN | CF₃ | 157 |
| 13 | 4-Cl-C₆H₄ | SCH₃ | CN | H | C—Cl | F | CF₃ | 152 |
| 14 | 4-Cl-C₆H₄ | SCH₃ | CN | H | N | Cl | CF₃ | 194 |
| 15 | 4-Br-C₆H₄ | SCH₃ | CN | H | C—NO₂ | NO₂ | CF₃ | 220 |
| 16 | 4-CF₃-C₆H₄ | SCH₃ | CN | H | C—NO₂ | NO₂ | CF₃ | 165 |
| 17 | 4-CH₃-C₆H₄ | SCH₃ | CN | H | C—NO₂ | NO₂ | CF₃ | 188 |
| 18 | 4-CH₃-C₆H₄ | SCH₃ | CN | H | C—Cl | Cl | CF₃ | 163 |
| 19 | 4-CH₃-C₆H₄ | SCH₃ | CN | H | N | Cl | CF₃ | 172 |
| 20 | 4-tBu-C₆H₄ | SCH₃ | CN | H | C—NO₂ | NO₂ | CF₃ | 160 |

TABLE 1-continued
(I-1)
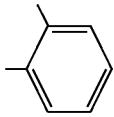
| Ex. No. | R¹ | R² | R³ | R⁴ | X | Y | Z | M.p. (°C.) |
|---|---|---|---|---|---|---|---|---|
| 21 | 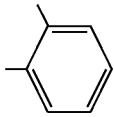 | SCH₃ | CN | H | C—NO₂ | NO₂ | CF₃ | 157 |
| 22 | 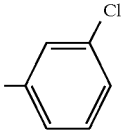 | SCH₃ | CN | H | C—Cl | Cl | CF₃ | 62 |
| 23 | 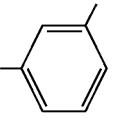 | SCH₃ | CN | H | C—NO₂ | NO₂ | CF₃ | 128 |
| 24 | 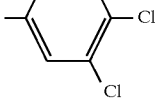 | SCH₃ | CN | H | C—Cl | Cl | CF₃ | Oil |
| 25 | 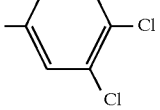 | SCH₃ | CN | H | C—NO₂ | NO₂ | CF₃ | 90 |
| 26 | 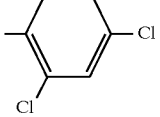 | SCH₃ | CN | H | N | Cl | CF₃ | 215 |
| 27 | 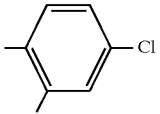 | SCH₃ | CN | H | C—NO₂ | NO₂ | CF₃ | 270 |
| 28 | 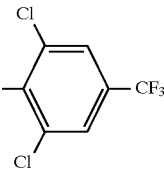 | SCH₃ | CN | H | C—Cl | Cl | CF₃ | 65 |
| 29 |  | SCH₃ | CN | H | C—NO₂ | NO₂ | CF₃ | 190 |

TABLE 1-continued (I-1)

| Ex. No. | R¹ | R² | R³ | R⁴ | X | Y | Z | M.p. (°C.) |
|---|---|---|---|---|---|---|---|---|
| 30 | 2,6-dichloro-4-(trifluoromethyl)phenyl | SCH₃ | CN | H | C—Cl | Cl | CF₃ | 165 |
| 31 | 2,6-dichloro-4-(trifluoromethyl)phenyl | SCH₃ | CN | H | N | Cl | CF₃ | 105 |
| 32 | 3-chloro-5-(trifluoromethyl)pyridin-2-yl | SCH₃ | CN | H | C—NO₂ | NO₂ | CF₃ | 178 |
| 33 | pyrimidin-2-yl | SCH₃ | CN | H | C—NO₂ | NO₂ | CF₃ | 212 |
| 34 | pyrimidin-2-yl | SCH₃ | CN | H | N | Cl | CF₃ | 173 |
| 35 | CH₃ | SCH₃ | CN | H | C—NO₂ | NO₂ | CF₃ | 150 |
| 36 | n-C₃H₇ | SCH₃ | CN | H | C—NO₂ | NO₂ | CF₃ | 149 |
| 37 | tBu | SCH₃ | CN | H | C—NO₂ | NO₂ | CF3 | 150/dec. |
| 38 | —H₂C-(3-trifluoromethylphenyl) | SCH₃ | CN | H | C—NO₂ | NO₂ | CF₃ | 112 |
| 39 | C₆H₅ | SOCH₃ | CN | H | C—NO₂ | NO₂ | CF₃ | 92 |
| 40 | C₆H₅ | SO₂CH₃ | CN | H | C—NO₂ | NO₂ | CF₃ | 172 |
| 41 | C₆H₅ | SCH₃ | CONH₂ | H | C—NO₂ | NO₂ | CF₃ | >240 |
| 42 | C₆H₅ | SCH₃ | CONH₂ | H | C—NO₂ | NO₂ | CF₃ | 198 |
| 43 | C₆H₅ | SCH₃ | CONH₂ | H | C—NO₂ | NO₂ | CF₃ | 112 |
| 44 | 2,6-dichloro-4-(trifluoromethyl)phenyl | H | CF₃ | H | C—NO₂ | NO₂ | CF₃ | 130 |

TABLE 1-continued (I-1)

| Ex. No. | R¹ | R² | R³ | R⁴ | X | Y | Z | M.p. (°C.) |
|---|---|---|---|---|---|---|---|---|
| 45 | 3,5-dichloropyridin-2-yl | H | CN | H | C—NO$_2$ | NO$_2$ | CF$_3$ | 150 |
| 46 | 3,5-dichloropyridin-2-yl | H | CN | H | C—NO$_2$ | NO$_2$ | CF$_3$ | 188 |
| 47 | 5-chloro-3-trifluoromethylpyridin-2-yl | H | CN | H | C—NO$_2$ | NO$_2$ | CF$_3$ | 170 |
| 48 | pyrimidin-2-yl | H | CN | H | C—NO$_2$ | NO$_2$ | CF$_3$ | 200 |
| 49 | 2-chloro-4-trifluoromethylphenyl | H | CN | H | C—Cl | Cl | CF$_3$ | 173 |
| 50 | 2-chloro-4-trifluoromethylphenyl | H | CN | H | N | Cl | CF$_3$ | 148 |
| 51 | CH$_3$ | H | CONH$_2$ | H | C—NO$_2$ | CF$_3$ | NO$_2$ | 217 |
| 52 | 2-chloro-4-trifluoromethylphenyl | H | CONH$_2$ | H | C—NO$_2$ | NO$_2$ | CF$_3$ | 200 |
| 53 | pyrimidin-2-yl | H | CO$_2$Et | H | C—NO$_2$ | NO$_2$ | CF$_3$ | 140 |
| 54 | 2,6-dichloro-4-trifluoromethylphenyl | SCH$_3$ | H | H | C—NO$_2$ | CF$_3$ | NO$_2$ | 137 |

TABLE 1-continued (I-1)

$$\text{pyrazole with } R^2, R^3 \text{ at 4,5; } N-R^1; \text{ NR}^4\text{-phenyl(X,Y,Z)}$$

| Ex. No. | R¹ | R² | R³ | R⁴ | X | Y | Z | M.p. (°C.) |
|---|---|---|---|---|---|---|---|---|
| 55 | 2,6-diCl-4-CF₃-phenyl | SOCH₃ | H | H | C—NO₂ | CF₃ | NO₂ | 230 |
| 56 | 2,6-diCl-4-CF₃-phenyl | CN | H | H | C—NO₂ | NO₂ | CF₃ | 171 |
| 57 | CH₃ | 2-thienyl | H | H | C—NO₂ | NO₂ | CF₃ | 199 |
| 58 | CH₃ | 4-Cl-phenyl | H | H | C—NO₂ | NO₂ | CF₃ | 224 |
| 59 | CH₃ | CH₃ | CN | H | N | Cl | CF₃ | 165 |
| 60 | CH₃ | C₂F₅ | CF₃ | H | C—NO₂ | NO₂ | CF₃ | 104 |
| 61 | CH₃ | C₂F₅ | CF₃ | H | C—NO₂ | CF₃ | NO₂ | 182 |
| 62 | CH₃ | C₂F₅ | CF₃ | H | C—Cl | CF₃ | CF₃ | 84 |
| 63 | C₆H₅ | C₂F₅ | CF₃ | H | C—NO₂ | NO₂ | CF₃ | 120 |
| 64 | C₆H₅ | C₂F₅ | CF₃ | H | C—NO₂ | CF₃ | NO₂ | 89 |
| 65 | 4-Cl-phenyl | C₂F₅ | CF₃ | H | C—NO₂ | NO₂ | CF₃ | Oil |
| 66 | 4-Cl-phenyl | C₂F₅ | CF₃ | H | C—NO₂ | CF₃ | NO₂ | 106 |
| 67 | 4-NO₂-phenyl | C₂F₅ | CF₃ | H | C—NO₂ | NO₂ | CF₃ | 60 |
| 68 | 2,6-diCl-4-CF₃-phenyl | C₂F₅ | CF₃ | H | C—NO₂ | NO₂ | CF₃ | 126 |
| 69 | CH₃ | H | H | H | N | Cl | CF₃ | 168 |
| 70 | C₆H₅ | H | H | H | C—NO₂ | NO₂ | CF₃ | 128 |

TABLE 1-continued (I-1)

$$\text{pyrazole-N(R}^4\text{)-aryl structure with R}^1, R^2, R^3, X, Y, Z$$

| Ex. No. | R¹ | R² | R³ | R⁴ | X | Y | Z | M.p. (°C.) |
|---|---|---|---|---|---|---|---|---|
| 71 | 2,6-diCl-4-CF₃-phenyl | CH₃ | SCF₂CH₃ | H | C—NO₂ | NO₂ | CF₃ | 169 |
| 72 | 2,6-diCl-4-CF₃-phenyl | CH₃ | SCH₂CF₃ | H | C—NO₂ | NO₂ | CF₃ | 198 |
| 73 | 2,6-diCl-4-CF₃-phenyl | CH₂OCH₃ | SCF₃ | H | C—NO₂ | NO₂ | CF₃ | 190 |
| 74 | 2,6-diCl-4-CF₃-phenyl | CH₂OCH₃ | SCF₂CH₃ | H | C—NO₂ | NO₂ | CF₃ | 148 |
| 75 | 3-Cl-5-CF₃-pyridin-2-yl | CH₃ | SCF₂CH₃ | H | C—NO₂ | NO₂ | CF₃ | 76 |
| 76 | C₆H₅ | CN | CN | H | C—NO₂ | NO₂ | CF₃ | 135 |
| 77 | C₆H₅ | CN | CN | H | C—NO₂ | CF₃ | NO₂ | 96 |
| 78 | 4-Cl-phenyl | CN | CN | H | C—NO₂ | NO₂ | CF₃ | 76 |
| 79 | 4-Cl-phenyl | CN | CN | H | C—NO₂ | CF₃ | NO₂ | 103 |
| 80 | 3,4-diCl-phenyl | CN | CN | H | C—NO₂ | NO₂ | CF₃ | 183 |

TABLE 1-continued
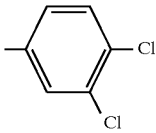
(I-1)
| Ex. No. | R¹ | R² | R³ | R⁴ | X | Y | Z | M.p. (°C.) |
|---|---|---|---|---|---|---|---|---|
| 81 | 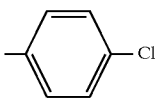 | CN | CN | H | C—NO₂ | CF₃ | NO₂ | 102 |
| 82 | 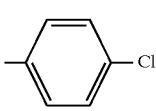 | CF₃ | CN | H | C—NO₂ | NO₂ | CF₃ | 68 |
| 83 | 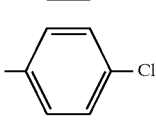 | CF₃ | CN | H | C—NO₂ | CF₃ | NO₂ | 78 |
| 84 | 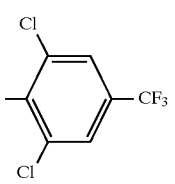 | CF₃ | CN | H | C—Cl | Cl | CF₃ | 129 |
| 85 | 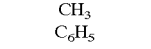 | H | CF₃ | CH₂OEt | C—NO₂ | NO₂ | CF₃ | 198 |
| 86 | CH₃ | C₂F₅ | CF₃ | CH₂OEt | C—NO₂ | CF₃ | NO₂ | |
| 87 | C₆H₅ | C₂F₅ | CF₃ | CH₂OEt | C—NO₂ | CF₃ | NO₂ | 90 |
| 88 | 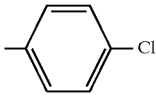 | C₂F₅ | CF₃ | CH₂OEt | C—NO₂ | NO₂ | CF₃ | Oil |
| 89 | 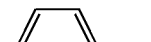 | H | CN | H | C—Cl | CN | CF₃ | Oil |
| 90 | C₆H₅ | CN | CN | H | C—Cl | Cl | CF₃ | 162 |
| 91 | 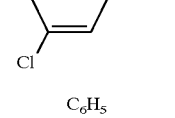 | CN | CN | H | C—Cl | Cl | CF₃ | 110 |
| 92 | 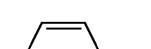 | CN | CN | H | C—Cl | Cl | OCF₃ | |
| 93 |  | CN | CN | H | C—Cl | Cl | CF₃ | |

TABLE 1-continued (I-1)

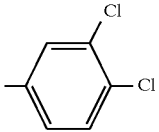

| Ex. No. | R¹ | R² | R³ | R⁴ | X | Y | Z | M.p. (°C.) |
|---|---|---|---|---|---|---|---|---|
| 94 | 3,4-dichlorophenyl | CN | CN | H | C—Cl | Cl | $CF_3$ | 104 |
| 95 | 4-bromophenyl | CN | CN | H | C—Cl | Cl | $CF_3$ | 182 |
| 96 | $C_6H_5$ | $CF_3$ | CN | H | $CNO_2$ | $NO_2$ | $CF_3$ | Oil |
| 97 | $C_6H_5$ | $CF_3$ | CN | H | $CNO_2$ | $CF_3$ | $NO_2$ | |
| 98 | $C_6H_5$ | $CF_3$ | CN | H | C—Cl | Cl | $CF_3$ | 120 |
| 99 | 4-bromophenyl | $CF_3$ | CN | H | C—Cl | Cl | $CF_3$ | |
| 100 | 4-trifluoromethylphenyl | $CF_3$ | CN | H | C—Cl | Cl | $CF_3$ | |
| 101 | 4-fluorophenyl | $CF_3$ | CN | H | C—Cl | Cl | $CF_3$ | |
| 102 | 4-chlorophenyl | $SO_2CH_3$ | CN | H | C—Cl | Cl | $CF_3$ | 87 |
| 103 | 4-chlorophenyl | $SOCH_3$ | CN | H | C—Cl | Cl | $CF_3$ | 71 |
| 104 | 4-chlorophenyl | $SCH_3$ | CN | H | C—Cl | Cl | $OCF_3$ | |
| 105 | 4-bromophenyl | $SCH_3$ | CN | H | C—Cl | Cl | $CF_3$ | 160 |
| 106 | 4-trifluoromethylphenyl | $SCH_3$ | CN | H | C—Cl | Cl | $CF_3$ | 161 |
| 107 | 3,4-dichlorophenyl | $SCH_3$ | CN | H | C—Cl | Cl | $CF_3$ | 142 |

TABLE 1-continued (I-1)

| Ex. No. | R¹ | R² | R³ | R⁴ | X | Y | Z | M.p. (°C.) |
|---|---|---|---|---|---|---|---|---|
| 108 | 4-Cl-C₆H₄- | CH₃ | CN | H | C—Cl | Cl | CF₃ | 75 |
| 109 | 4-Cl-C₆H₄- | H | CN | H | C—Cl | Cl | CF₃ | 62 |
| 110 | CH₃ | SCH₃ | CN | H | C—Cl | Cl | CF₃ | |
| 111 | tBu | SCH₃ | CN | H | C—Cl | Cl | CF₃ | |
| 112 | CH₃ | 4-Cl-C₆H₄- | CN | H | C—Cl | Cl | CF₃ | |
| 113 | 4-Cl-C₆H₄- | 4-Cl-C₆H₄- | CN | H | C—Cl | Cl | CF₃ | |
| 114 | N=C(CF₃)-S-C(CH₃)=N | SCH₃ | CN | H | C—Cl | Cl | CF₃ | |
| 115 | N=C(CF₃)-S-C(CH₃)=N | H | CN | H | C—Cl | Cl | CF₃ | |
| 116 | N=C(CF₃)-S-C(CH₃)=N | CN | CN | H | C—Cl | Cl | CF₃ | |
| 117 | CH₃ | C₂F₅ | CF₃ | CH₃ | C—NO₂ | NO₂ | CF₃ | Oil |
| 118 | CH₃ | C₂F₅ | CF₃ | —C(O)—C₆H₅ | C—NO₂ | NO₂ | CF₃ | |
| 119 | CH₃ | C₂F₅ | CF₃ | —C(O)—CH₃ | C—NO₂ | NO₂ | CF₃ | |
| 120 | CH₃ | C₂F₅ | CF₃ | —SO₂N(CH₃)₂ | C—NO₂ | NO₂ | CF₃ | |
| 121 | 2,6-Cl₂-4-CF₃-C₆H₂- | C₂F₅ | CF₃ | H | C—NO₂ | CF₃ | NO₂ | 115 |
| 122 | 4-NO₂-C₆H₄- | C₂F₅ | CF₃ | H | C—NO₂ | CF₃ | NO₂ | 123 |
| 123 | tC₄H₉ | CN | CN | H | C—Cl | Cl | CF₃ | 173 |

TABLE 1-continued (I-1)

| Ex. No. | R¹ | R² | R³ | R⁴ | X | Y | Z | M.p. (°C.) |
|---|---|---|---|---|---|---|---|---|
| 124 | 4-Ph-C₆H₄- | CN | CN | H | C—Cl | Cl | CF₃ | 220 |
| 125 | 4-OPh-C₆H₄- | CN | CN | H | C—Cl | Cl | CF₃ | 184 |
| 126 | 3-Cl-C₆H₄- | CN | CN | H | C—Cl | Cl | CF₃ | 143 |
| 127 | 3-Br-C₆H₄- | CN | CN | H | C—Cl | Cl | CF₃ | 135 |
| 128 | 3-CF₃-C₆H₄- | CN | CN | H | C—Cl | Cl | CF₃ | 147 |
| 129 | 3-CHF₂-C₆H₄- | CN | CN | H | C—Cl | Cl | CF₃ | 144 |
| 130 | 3-SCH₃-C₆H₄- | CN | CN | H | C—Cl | Cl | CF₃ | 155 |
| 131 | 3-Ph-C₆H₄- | CN | CN | H | C—Cl | Cl | CF₃ | 90 |
| 132 | 3,4-Cl₂-C₆H₃- | CN | CN | H | C—Cl | Cl | CF₃ | 73 |
| 133 | 4-CH₃-C₆H₄- | CN | CN | H | C—Cl | Cl | CF₃ | 68 |

TABLE 1-continued (I-1)

| Ex. No. | R¹ | R² | R³ | R⁴ | X | Y | Z | M.p. (°C.) |
|---|---|---|---|---|---|---|---|---|
| 134 | 4-CF₃-C₆H₄ | CN | CN | H | C—Cl | Cl | CF₃ | 186 |
| 135 | 4-OCF₃-C₆H₄ | CN | CN | H | C—Cl | Cl | CF₃ | 136 |
| 136 | 4-F-C₆H₄ | CN | CN | H | C—Cl | Cl | CF₃ | 113 |
| 137 | 4-iPr-C₆H₄ | CN | CN | H | C—Cl | Cl | CF₃ | 78 |
| 138 | 3-Cl-C₆H₄ | CN | CN | H | C—Cl | Cl | CF₃ | 76 |
| 139 | 4-Ph-C₆H₄ | CF₃ | CN | H | C—Cl | Cl | CF₃ | 84 |
| 140 | 4-OPh-C₆H₄ | CF₃ | CN | H | C—Cl | Cl | CF₃ | 148 |
| 141 | 3-Cl-C₆H₄ | CF₃ | CN | H | C—Cl | Cl | CF₃ | 103 |
| 142 | 3-Br-C₆H₄ | CF₃ | CN | H | C—Cl | Cl | CF₃ | 88 |
| 143 | 2-Cl-C₆H₄ | CF₃ | CN | H | C—Cl | Cl | CF₃ | 103 |
| 144 | 2,4-Cl₂-C₆H₃ | CF₃ | CN | H | C—Cl | Cl | CF₃ | 67 |

TABLE 1-continued (I-1)

| Ex. No. | R¹ | R² | R³ | R⁴ | X | Y | Z | M.p. (°C.) |
|---|---|---|---|---|---|---|---|---|
| 145 | CH₃ | CH₃ | CN | H | C—NO₂ | NO₂ | CF₃ | 174 |
| 146 | tBu | CF₃ | CN | H | C—Cl | Cl | CF₃ | |
| 147 | 4-OCH₃-C₆H₄ | CF₃ | CN | H | C—Cl | Cl | CF₃ | |
| 148 | 2-CH₃-4-Cl-C₆H₃ | CF₃ | CN | H | C—Cl | Cl | CF₃ | |
| 149 | 3,4-Cl₂-C₆H₃ | CF₃ | CN | H | C—Cl | Cl | CF₃ | |
| 150 | 4-CH₃-C₆H₄ | CF₃ | CN | H | C—Cl | Cl | CF₃ | |
| 151 | 2,6-(CH₃)₂-C₆H₃ | CF₃ | CN | H | C—Cl | Cl | CF₃ | |
| 152 | 2,3-Cl₂-C₆H₃ | CF₃ | CN | H | C—Cl | Cl | CF₃ | |
| 153 | C₆H₅ | C₂F₅ | CN | H | C—Cl | Cl | CF₃ | |
| 154 | 4-OCH₃-C₆H₄ | CN | CN | H | C—Cl | Cl | CF₃ | |
| 155 | 2-CH₃-5-Cl-C₆H₃ | CN | CN | H | C—Cl | Cl | CF₃ | |

TABLE 1-continued

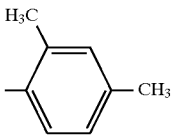

(I-1)

| Ex. No. | R¹ | R² | R³ | R⁴ | X | Y | Z | M.p. (°C.) |
|---|---|---|---|---|---|---|---|---|
| 156 | 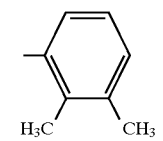 | CN | CN | H | C—Cl | Cl | $CF_3$ | |
| 157 | 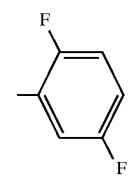 | CN | CN | H | C—Cl | Cl | $CF_3$ | |
| 158 | 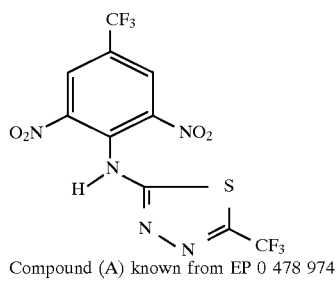 | CN | CN | H | C—Cl | Cl | $CF_3$ | |
| 159 | —$(CH_2)_3CH_3$ | CN | CN | H | C—Cl | Cl | $CF_3$ | |
| 160 | —$(CH_2)_2OH$ | CN | CN | H | C—Cl | Cl | $CF_3$ | |
| 161 | —$CH_2CF_3$ | CN | CN | H | C—Cl | Cl | $CF_3$ | |
| 162 | —$CH_3$ | CN | CN | H | C—Cl | Cl | $CF_3$ | |
| 163 | —$C_2H_5$ | CN | CN | H | C—Cl | Cl | $CF_3$ | |
| 164 | —$CH_2Ph$ | CN | CN | H | C—Cl | Cl | $CF_3$ | |

*$C_6H_5$ = phenyl = Ph
Bu = butyl
Pr = propyl
Et = ethyl

Use Examples

In the use examples which follow, the compounds listed below were employed as comparison substances:

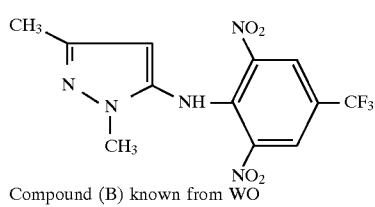

Compound (A) known from EP 0 478 974

Compound (B) known from WO

Example A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the desired period of time, the destruction in % is determined. 100% means that all the beetle larvae have been killed; 0% means that none of the beetle larvae have been killed.

In this test, a destruction rate of 100% was shown, after 3 days, for example by the compounds of Preparation Examples 10, 11, 37, 44, 47, 60, 71, 73 and 75 at an exemplary active compound concentration of 0.01%, while the prior-art compounds (A) and (B) resulted in no destruction.

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the diamond-back moth (*Plutella maculipennis*), while the leaves are still moist.

After the desired period of time, the destruction in % is determined. 100% means that all the caterpillars have been killed; 0% means that none of the caterpillars have been killed.

In this test, a destruction rate of at least 80% was shown, after 3 days, for example by the compounds of Preparation Examples 13, 60, 61 and 75 at an exemplary active compound concentration of 0.001%, while the prior-art compounds (A) and (B) resulted in no destruction.

Example C

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the fall armyworm (*Spodoptera frugiperda*), while the leaves are still moist.

After the desired period of time, the destruction in % is determined. 100% means that all the caterpillars have been killed; 0% means that none of the caterpillars have been killed.

In this test, a destruction rate of 100% was shown, after 3 days, for example by the compounds of Preparation Examples 8, 11, 12, 13, 28, 30, 31, 32, 60, 74 and 89 at an exemplary active compound concentration of 0.1%, while the prior-art compound (A) resulted in no destruction.

Example D

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of the active compound of the desired concentration and are infested with the green rice leafhopper (*Nephotettix cincticeps*) while the leaves are still moist.

After the desired period of time, the destruction in % is determined. 100% means that all the leafhoppers have been killed; 0% means that none of the leafhoppers have been killed.

In this test, a destruction rate of 100% was shown, after 6 days, for example by the compounds of Preparation Examples 22, 60 and 63 at an exemplary active compound concentration of 0.1%, while the prior-art compounds (A) and (B) resulted in no destruction.

Example E

Tetranychus test (OP resistant)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are severely infested with all development stages of the greenhouse red spider mite (*Tetranychus urticae*) are dipped into a preparation of the active compound of the desired concentration.

After the desired period of time, the effect in percent is determined. 100% means that all the spider mites have been killed; 0% means that none of the spider mites have been killed.

In this test, a destruction rate of 100% was shown, after 7 days, for example by the compounds of Preparation Examples 8, 13, 28 and 60 at an exemplary active compound concentration of 0.01%, while the prior-art compound (A) resulted in no destruction.

Example F

Plasmopara test (vines)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20 to 22° C. and 100% relative atmospheric humidity for 1 day. The plants are then placed in a greenhouse at 21° C. and 90% atmospheric humidity for 5 days. The plants are then moistened and placed in a humidity chamber for 1 day.

Evaluation is carried out 6 days after the inoculation.

In this test, a degree of effectiveness of at least 90% was shown, for example, by the compounds of Preparation Examples 7, 16, 36, 37 and 60 at an exemplary active compound concentration of 10 ppm.

Example G

Podosphaera test (apple)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew (*Podosphaera leucotricha*).

The plants are then placed in a greenhouse at 23° C. and a relative atmospheric humidity of about 70%.

Evaluation is carried out 10 days after the inoculation.

In this test, a degree of effectiveness of at least 96% was shown, for example, by the compounds of Preparation Examples 44, 10, 37 and 60 at an exemplary active compound concentration of 25 ppm.

Example H

Venturia test (apple)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a degree of effectiveness of at least 99% was shown, for example, by the compounds of Preparation Examples 37 and 60 at an exemplary active compound concentration of 10 ppm.

Example I

Test with *Lucilia cuprina* resistant larvae

Emulsifier: 35 parts by weight of ethylene glycol monomethyl ether 35 parts by weight of nonyl phenol polyglycol ether To produce a suitable preparation of active compounds three parts by weight of active compound are mixed with seven parts by weight of the above-mentioned solvent mixture and the concentrate thus obtained is diluted with water to the concentration desired in each case.

About 20 *Lucilia cuprina* resistant larvae are introduced into a test tube which contains about 1 cm² of horse meat and 0.5 ml of the preparation of active compound. After 24 hours the degree of destruction is determined.

100% means that all the larvae have been killed, 0% means that none of the larvae have been killed.

In this test, a degree of destruction of 100% was shown, for example, by the compound of Preparation Example 60 at an exemplary active compound concentration of 1000 ppm.

Example J

Fly test

Test animals: *Musca domestica*, strain WHO (N)

Solvent: 35 parts by weight of ethylene glycol monomethyl ether

Emulsifier: 35 parts by weight of nonylphenol polyglycol ether

To produce a suitable formulation, three parts by weight of active compound are mixed with seven parts of the above-mentioned solvent/emulsifier mixture, and the resulting emulsion concentrate is diluted with water to the particular concentration desired.

2 ml of this preparation of active compound are pipetted onto filter paper discs (Ø 9.5 cm) located in Petri dishes of suitable size. After the filter discs have dried, 25 test animals are transferred into the Petri dishes and covered.

After 24 hours, the effectiveness of the preparation of active compound is determined. The effectiveness is expressed as a percentage. 100% means that all flies have been killed; 0% means that none of the flies have been killed.

In this test, an effectiveness of 100% was shown, for example, by the compound of Preparation Example 60 at an exemplary active compound concentration of 1000 ppm.

Example K

Cockroach test

Test animals: *Periplaneta americana*

Solvent: 35 parts by weight of ethylene glycol monomethyl ether

Emulsifier: 35 parts by weight of nonylphenol polyglycol ether

To produce a suitable formulation, three parts by weight of active compound are mixed with seven parts of the abovementioned solvent/emulsifier mixture, and the resulting emulsion concentrate is diluted with water to the particular concentration desired.

2 ml of this preparation of active compound are pipetted onto filter paper discs (Ø 9.5 cm) located in Petri dishes of a suitable size. After the filter discs have dried, 5 test animals in B. germanica or P. americana are transferred and covered.

After 3 days, the effectiveness of the preparation of active compound is determined. The effectiveness is expressed as a percentage. 100% means that all cockroaches have been killed; 0% means that none of the cockroaches have been killed.

At an exemplary concentration of 1000 ppm, the active compound of Preparation Example 60 results in a destruction rate of 100%.

We claim:

1. A compound of the formula

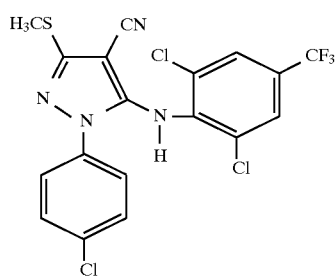

2. A compound of the formula

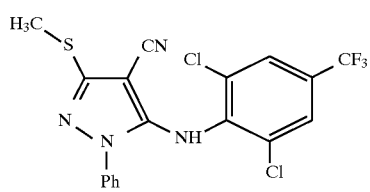

3. A compound of the formula

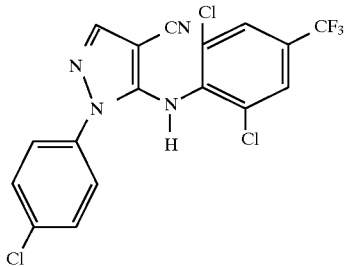

4. A pesticidal composition which comprises a compound according to claim 1 and an inert carrier.

5. A pesticidal composition which comprises a compound according to claim 2 and an inert carrier.

6. A pesticidal composition which comprises a compound according to claim 3 and an inert carrier.

7. A method of combating animal pest which comprises applying a compound according to claim 1 to said pests or to an environment where they reside.

8. A method of combating animal pest which comprises applying a compound accordint to claim 2 to said pest or to an envionment where they reside.

9. A method of combating animal pest which comprises applying a compound accordint to claim 3 to said pest or to an envionment where they reside.

* * * * *